(12) United States Patent
Kassab

(10) Patent No.: US 7,818,053 B2
(45) Date of Patent: Oct. 19, 2010

(54) DEVICES, SYSTEMS AND METHODS FOR PLAQUE TYPE DETERMINATION

(75) Inventor: Ghassan S. Kassab, Newport Coast, CA (US)

(73) Assignee: DTherapeutics, LLC, Zionsville, IN (US)

( * ) Notice: Subject to any disclaimer, the term of this patent is extended or adjusted under 35 U.S.C. 154(b) by 1464 days.

(21) Appl. No.: 11/063,836

(22) Filed: Feb. 23, 2005

(65) Prior Publication Data

US 2005/0203434 A1 Sep. 15, 2005

Related U.S. Application Data

(63) Continuation-in-part of application No. 10/782,149, filed on Feb. 19, 2004, now Pat. No. 7,454,244.

(60) Provisional application No. 60/449,266, filed on Feb. 21, 2003, provisional application No. 60/493,145, filed on Aug. 7, 2003, provisional application No. 60/502,139, filed on Sep. 11, 2003.

(51) Int. Cl.
*A61B 5/05* (2006.01)

(52) U.S. Cl. ....................................... 600/547

(58) Field of Classification Search .................. 600/547, 600/481, 454, 505, 506, 526, 587, 486, 561, 600/483; 606/41, 192, 194, 198; 128/898; 424/439
See application file for complete search history.

(56) References Cited

U.S. PATENT DOCUMENTS

| 3,896,373 | A | | 7/1975 | Zelby |
|---|---|---|---|---|
| 4,587,975 | A | | 5/1986 | Salo et al. |
| 4,840,182 | A | | 6/1989 | Carlson |
| 4,957,110 | A | | 9/1990 | Vogel et al. |
| 5,058,583 | A | | 10/1991 | Geddes et al. |
| 5,125,410 | A | | 6/1992 | Misono et al. |
| 5,233,994 | A | | 8/1993 | Shmulewitz |
| 5,366,443 | A | | 11/1994 | Eggers et al. |
| 5,453,576 | A | * | 9/1995 | Krivitski ..................... 600/481 |
| 5,665,103 | A | | 9/1997 | Lafontaine et al. |
| 5,971,933 | A | | 10/1999 | Schlueter et al. |

(Continued)

FOREIGN PATENT DOCUMENTS

EP 1 025 805 A1 8/2000

(Continued)

OTHER PUBLICATIONS

International Searching Authority, International Search Report for PCT Application Serial No. PCT/ US06/05985, Aug. 8, 2007.

(Continued)

*Primary Examiner*—Max Hindenburg
*Assistant Examiner*—Brian Szmal
(74) *Attorney, Agent, or Firm*—Ice Miller LLP

(57) ABSTRACT

Devices, systems and methods are disclosed for determining the composition of a plaque at a plaque site, which could be inside a blood vessel. Through a combination of fluid injection with different conductivities and measurement of the resultant conductances, a parallel tissue conductance measure is obtained that assists in determining the composition of the site plaque. Lower parallel conductance levels are determinative of a higher lipid and/or fatty plaque, which is a type that may break out of its position and cause organ injury or death.

31 Claims, 8 Drawing Sheets

U.S. PATENT DOCUMENTS

| | | | |
|---|---|---|---|
| 6,112,115 | A | 8/2000 | Feldman et al. |
| 6,165,977 | A | 12/2000 | Mochly-Rosen |
| 6,187,744 | B1 | 2/2001 | Rooney |
| 6,191,136 | B1 | 2/2001 | Marban |
| 6,270,493 | B1 | 8/2001 | Lalonde et al. |
| 6,325,762 | B1 | 12/2001 | Tjin |
| 6,354,999 | B1 | 3/2002 | Dgany et al. |
| 6,360,123 | B1 | 3/2002 | Kimchi et al. |
| 6,398,738 | B1 | 6/2002 | Millar |
| 6,406,422 | B1 | 6/2002 | Landesberg |
| 6,471,656 | B1 | 10/2002 | Shalman et al. |
| 6,494,832 | B1 | 12/2002 | Feldman et al. |
| 6,511,413 | B2 | 1/2003 | Landesberg |
| 6,545,678 | B1 | 4/2003 | Ohazama |
| 6,569,862 | B1 | 5/2003 | Marban |
| 6,663,661 | B2 | 12/2003 | Boneau |
| 6,666,828 | B2 | 12/2003 | Greco et al. |
| 6,926,674 | B2 | 8/2005 | Tenerz et al. |
| 6,939,313 | B2 | 9/2005 | Saadat |
| 7,069,072 | B2 | 6/2006 | Jansen et al. |
| 7,141,019 | B2 | 11/2006 | Pearlman |
| 7,169,107 | B2 | 1/2007 | Jersey-Willuhn et al. |
| 7,189,208 | B1 | 3/2007 | Beatty et al. |
| 7,326,241 | B2 | 2/2008 | Jang |
| 2003/0149368 | A1* | 8/2003 | Hennemann et al. ........ 600/483 |
| 2003/0195504 | A1* | 10/2003 | Tallarida et al. .............. 606/41 |
| 2004/0254495 | A1* | 12/2004 | Mabary et al. ............. 600/547 |

FOREIGN PATENT DOCUMENTS

| | | |
|---|---|---|
| WO | WO 98/35611 A1 | 8/1998 |
| WO | WO 02/19905 | 3/2002 |
| WO | WO 02/085442 A1 | 10/2002 |
| WO | WO 03/092495 A1 | 11/2003 |

OTHER PUBLICATIONS

International Searching Authority, Written Opinion of the International Searching Authority for PCT Application Serial No. PCT/US06/05985, Aug. 8, 2007.

Supplementary European Search Report for EP Application Serial No. EP 04 71 2383 to Electro-Cat, LLC, dated Aug. 6, 2007.

PCT/US04/04828, PCT Search Report and Written Opinion, dated Jul. 6, 2005.

Hoekstein and Inbar, "Cardiac Stroke Volume Estimation from Two Electrodes Electrical Impedance Measurements." Technion Department of Electrical Engineering Publication EE Pub No. 911, Feb. 1994.

L. Komet, J.R.C. Jansen, E.J. Gussenhoven, M.R. Hardeman, A.P.G. Hoeks and A. Versprille, "Conductamce Method for the Measurement of Cross-Sectional Areas of the Aorta," Annals of Biomedical Engineering, vol. 27, pp. 141-150, 1999.

Douglas A. Hettrick, Joespeh Battocletti, James Ackmann, and David C. Warltier, "Finite Element Model Determination of Correction Factors Used for Measurement of Aorta Diameter via Conductance," Annals of Biomedical Engineering, vol. 27, pp. 151-159, 1999.

Douglas A. Hettrick, Joseph Battocletti, James Ackmann, John Linehan,a nd David C. Warltier, "In Vivo Measurement of Real-Time Aortic Segmental Volume Using the Conductance Catheter," Annals of Biomedical Engineering, vol. 26, pp. 431-440, 1998.

* cited by examiner

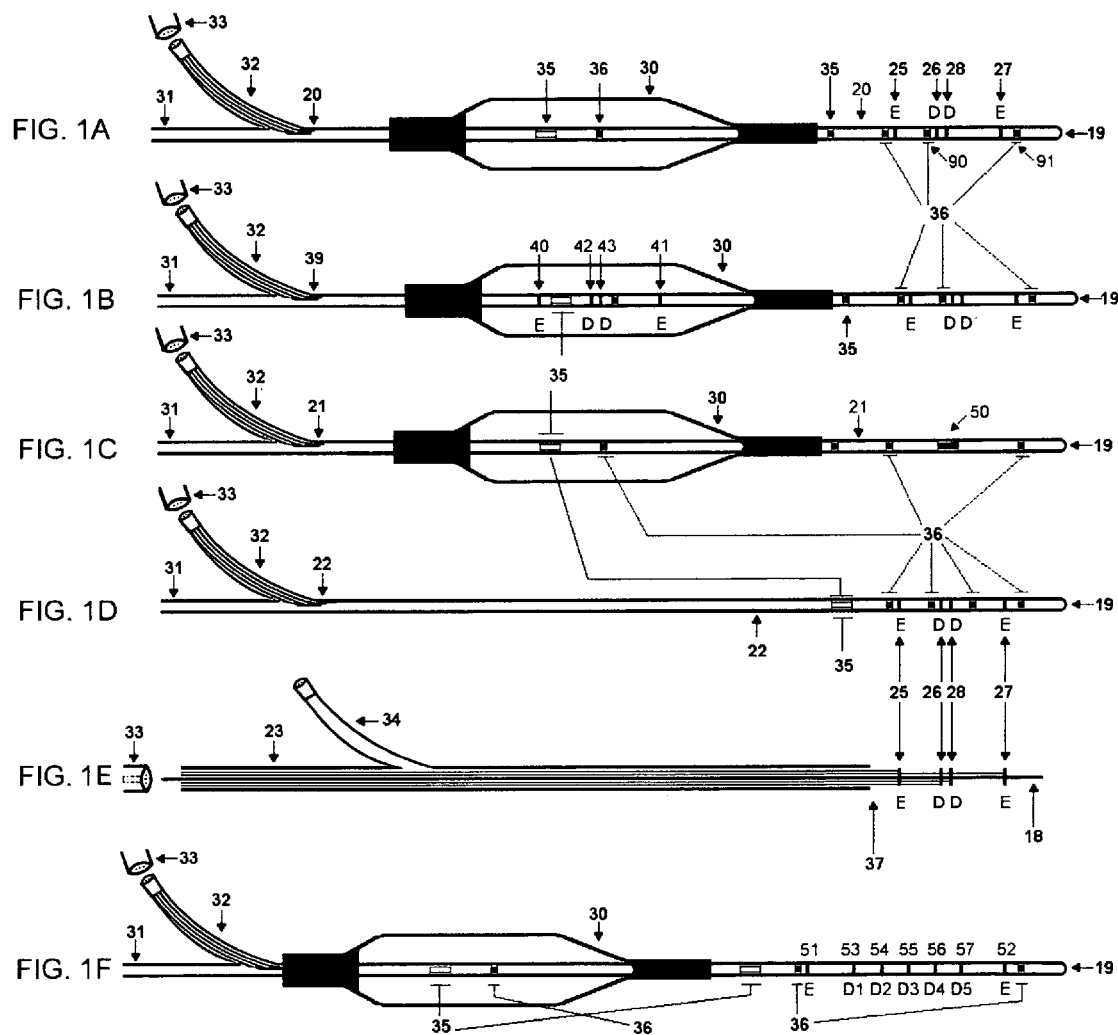

DEVICES, SYSTEMS AND METHODS FOR PLAQUE TYPE DETERMINATION

This U.S. Utility patent application is a continuation-in-part of U.S. patent application Ser. No. 10/782,149, filed Feb. 19, 2004; now U.S. Pat. No. 7,454,244 which claims priority to U.S. Provisional Patent Application Ser. No. 60/449,266, filed Feb. 21, 2003, and to U.S. Provisional Patent Application Ser. No. 60/493,145, filed Aug. 7, 2003, and to U.S. Provisional Patent Application Ser. No. 60/502,139, filed Sep. 11, 2003, the contents of each of which are hereby incorporated by reference in their entirety into this disclosure.

BACKGROUND OF THE INVENTION

1. Field of the Invention

The present invention relates generally to medical diagnostics and treatment. More particularly, the present invention relates to devices, systems and methods for determination of plaque type in vessels.

2. Background of the Invention

Coronary heart disease (CHD) is commonly caused by atherosclerotic narrowing of the coronary arteries and is likely to produce angina pectoris, heart attacks or a combination. CHD caused 466,101 deaths in the USA in 1997 and is one of the leading causes of death in America today. Approximately 12 million people alive today have a history of heart attack, angina pectoris or the combination. The breakdown for males and females is about 49% and 51%, respectively. This year, an estimated 1.1 million Americans will have a new or recurrent coronary attack, and more than 40% of the people experiencing these attacks will die as a result. About 225,000 people a year die of coronary attack without being hospitalized. These are sudden deaths caused by cardiac arrest, usually resulting from ventricular fibrillation. More than 400,000 Americans and 800,000 patients worldwide undergo a non-surgical coronary artery interventional procedure each year. Although only introduced in the 1990s, in some clinics, intra-coronary stents are used in 90% of these patients.

One common type of coronary artery disease is atherosclerosis, which is a systemic inflammatory disease of the vessel wall that affects multiple arterial beds, such as aorta, carotid and peripheral arteries, and causes multiple coronary artery lesions and plaques. Atherosclerotic plaques typically include connective tissue, extracellular matrix (including collagen, proteoglycans, and fibronectin elastic fibers), lipid (crystalline cholesterol, cholesterol esters and phospholipids), and cells such as monocyte-derived macrophages, T lymphocytes, and smooth muscles cells. A wide range of plaques occurs pathologically with varying composition of these components.

A process called "positive remodeling" occurs early on during the development of atherosclerosis in coronary artery disease (CAD) where the lumen cross-sectional area (CSA) stays relatively normal because of the expansion of external elastic membrane and the enlargement of the outer CSA. However, as CAD progresses, there is no further increase in the external diameter of the external elastic membrane. Instead, the plaque begins to impinge into the lumen and decreases the lumen CSA in a process called "negative remodeling".

Evidence shows that that a non-significant coronary atherosclerotic plaque (typically <50% stenosis) can rupture and produce myocardial infarct even before it produces significant lumen narrowing if the plaque has a particular composition. For example, a plaque with a high concentration of lipid and a thin fibrous cap may be easily sheared or ruptured and is referred to as a "vulnerable" plaque. In contrast, "white" plaques are less likely to rupture because the increased fibrous content over the lipid core provides stability ("stable" plaque). A large lipid core (typically >40%) rich in cholesterol is at a high risk for rupture and is considered a "vulnerable" plaque. In summary, plaque composition appears to determine the risk of acute coronary syndrome more so than the standard degree of stenosis because a higher lipid core is a basic characteristic of a higher risk plaque."

Conventionally, angiography has been used to visualize and characterize atherosclerotic plaque in coronary arteries. Because of the recent finding that plaque composition, rather than severity of stenosis, determines the risk for acute coronary syndromes, newer imaging modalities are required to distinguish between and determine the composition of "stable" and "vulnerable" plaques. Although a number of invasive and noninvasive imaging techniques are available to assess atherosclerotic vessels, most of the standard techniques identify luminal diameter, stenosis, wall thickness and plaque volume. To date, there is no standard method that can characterize plaque composition (e.g., lipid, fibrous, calcium, or thrombus) and therefore there is no routine and reliable method to identify the higher risk plaques.

Noninvasive techniques for evaluation of plaque composition include magnetic resonance imaging (MRI). However, MRI lacks the sufficient spatial resolution for characterization of the atherosclerotic lesion in the coronary vessel. Minimally invasive techniques for evaluation of plaque composition include intravascular ultrasound (IVUS), optical coherence tomography (OCT), raman and infrared spectroscopy. Thermography is also a catheter-based technique used to detect the vulnerable plaques on the basis of temperature difference caused by the inflammation in the plaque. Using the various catheter-based techniques requires a first step of advancement of an IVUS, OCT, or thermography catheter and then withdrawal of the catheter before coronary angioplasty thereby adding additional time and steps to the stent procedure. Furthermore, these devices require expensive machinery and parts to operate. This adds significant cost and time and more risk to the procedure.

Thus, a need exists in the art for an alternative to the conventional methods of determining plaque type. A further need exist for a reliable, accurate and minimally invasive system or technique of determining a plaque type or composition within a given blood vessel.

SUMMARY OF THE INVENTION

The present invention provides devices, systems and methods for determining the type and/or composition of a plaque that may be engaged within a blood vessel. The term "vessel," as used herein, refers generally to any hollow, tubular, or luminal organ. Such techniques according to the present invention are minimally invasive, accurate, reliable and easily reproducible. The understanding of a plaque type or composition allows a health care professional to better assess the risks of the plaque dislodging from its position and promoting infarct downstream. As discussed above, such determination of plaque information allows for removal or other disintegration of a smaller plaque that may otherwise not be of concern under conventional thought merely because of its smaller size. However, smaller plaques, depending on their composition, are potentially lethal, and this invention serves to decrease the ill effects of such plaques by assessing their type and composition when they are still "too small" to be of concern for standard medical diagnoses.

In one particular embodiment of the present invention, a device is disclosed for assessing composition of a plaque as determined by resistance to flow of electrical currents through the plaque. The device includes an elongated body having a longitudinal axis extending from a proximal end to a distal end, the body having a lumen along the longitudinal axis and enabling introduction of the distal end near a plaque at a plaque site; a first excitation electrode and a second excitation electrode along the longitudinal axis, both located near the distal end; and a first detection electrode and a second detection electrode located along the longitudinal axis and in between the first and second excitation electrodes; wherein at least one of the first and second excitation electrodes is in communication with a current source, thereby enabling a supply of electrical current to the plaque at the plaque site, thereby enabling measurement of two or more conductance values at the plaque site by the detection electrodes, and thereby enabling calculation of parallel tissue conductance at the plaque site, whereby tissue conductance is the inverse of resistance to current flow, which depends on the composition of the plaque.

In another embodiment, the present invention is a device for assessing composition of a plaque. The device includes an elongated body having a lumen therethrough along its longitudinal length; a pair of excitation electrodes located on the elongated body; and a pair of detection electrodes located in between the pair of excitation electrodes such that a distance between one detection electrode and its adjacent excitation electrode is equal to the distance between the other detection electrode and its adjacent excitation electrode; wherein at least one excitation electrode is in communication with a current source, thereby enabling a supply of electrical current to the plaque at the plaque site, and enabling measurement of two or more conductance values at the plaque site by the detection electrodes, resulting in an assessment of the composition of the plaque.

In yet another embodiment, the present invention is a device for assessing composition of a plaque. The device includes an elongated body having a lumen therethrough along its longitudinal length; a pair of excitation electrodes located on the elongated body; and a pair of detection electrodes located in between the pair of excitation electrodes; wherein at least one excitation electrode is in communication with a current source, thereby enabling a supply of electrical current to the plaque at the plaque site, and enabling measurement of two or more conductance values at the plaque site by the detection electrodes, resulting in a determination of the plaque as being at least partially fatty if the value as determined by Equation [6] is less than 70%.

In another embodiment, a catheter is disclosed for assessing composition of a plaque. The catheter includes an elongated body having a lumen therethrough along its longitudinal length; a pair of excitation electrodes located on the elongated body; and a pair of detection electrodes located in between the pair of excitation electrodes such that a distance between one detection electrode and its adjacent excitation electrode is equal to the distance between the other detection electrode and its adjacent excitation electrode; wherein when two solutions of differing conductive concentrations are introduced to a plaque site through the lumen of the elongated body at different times, two conductance measurements are made by the detection electrodes, resulting in a calculation of parallel tissue conductance at the plaque site to determine plaque composition.

In yet another embodiment, a catheter is disclosed for assessing composition of a plaque. The catheter including an elongated body having a proximal end and a distal end and a lumen therethrough; a second body that terminates at the elongated body at a point between the proximal end and the distal end, and having a lumen that joins the lumen of the elongated body; a pair of excitation electrodes located at a distal end of the elongated body; and a pair of detection electrodes located in between the pair of excitation electrodes; wherein when two solutions of differing conductive concentrations are introduced to a plaque site, located near the distal end of the elongated body, through the lumen of the second body, two conductance measurements are made by the detection electrodes, resulting in a calculation of parallel tissue conductance at the plaque site to determine plaque composition.

In another embodiment, a system is disclosed for assessing composition of a plaque as determined by resistance to flow of electrical currents through the plaque. The system includes an elongate wire having a longitudinal axis with a proximal end and a distal end; a catheter comprising an elongate tube extending from a proximal tube end to a distal tube end, the tube having a lumen and surrounding the wire coaxially; a first excitation electrode and a second excitation electrode located along the longitudinal axis of the wire near the distal wire end; and a first detection electrode and a second detection electrode along the longitudinal axis of the wire and in between the first and second excitation electrodes, wherein at least one of the first and second excitation electrodes is in communication with a current source, thereby enabling a supply of electrical current to a plaque, thereby enabling measurement of two or more conductance values at the plaque by the detection electrodes, and thereby enabling calculation of tissue conductance at the plaque site, whereby tissue conductance is the inverse of resistance to current flow, which depends on the composition of the plaque.

In yet another exemplary embodiment, a system is disclosed for measuring conductance of a plaque site to determine its composition. The system includes a catheter assembly; a solution delivery source for injecting a solution through the catheter assembly and into a plaque site; a current source; and a data acquisition and processing system that receives conductance data from the catheter assembly and determines the conductance value at the plaque site, whereby plaque conductance is the inverse of resistance to current flow, which depends on the composition of the plaque.

In one embodiment, a system is disclosed for determining the composition of a targeted plaque in a plaque site. The system includes a catheter having a proximal end and a distal end, the catheter further comprising a suction/infusion port near the distal end; a solution delivery source for injecting a solution through the catheter, through the suction/infusion port and into a plaque site containing a plaque; a current source; and a data acquisition and processing system that receives conductance data from the catheter and measures the conductance of the plaque site, thereby determining the composition of the plaque.

In yet another embodiment, a method is disclosed for measuring the composition of a targeted plaque in a plaque site. The method includes introducing a catheter into the plaque site; providing electrical current flow to the plaque site through the catheter; injecting a first solution of a first compound having a first concentration into the treatment site; measuring a first conductance value at the plaque site; injecting a second solution of a second compound having a second concentration into the plaque site, wherein the second concentration does not equal the first concentration; measuring a second conductance value at the plaque site; and determining the composition of the plaque based on the first and second conductance values and the conductivity values of the first and second compounds.

In another embodiment, a method is disclosed for measuring the composition of a plaque. The method includes introducing a catheter into the plaque site; injecting a first solution of a first compound having a first concentration into the treatment site; measuring a first conductance value at the plaque site; injecting a second solution of a second compound having a different concentration into the plaque site; measuring a second conductance value at the plaque site; and determining the composition of the plaque based on the first and second conductance values and the conductivity values of the first and second compounds; wherein a plaque is deemed as partially fatty if the value as determined by Equation [6] is less than 70%.

BRIEF DESCRIPTION OF THE DRAWINGS

FIG. 1A illustrates a balloon catheter according to an exemplary embodiment of the present invention having impedance-measuring electrodes supported in a distal position with respect to the stenting balloon.

FIG. 1B illustrates a balloon catheter according to another exemplary embodiment of the present invention having impedance-measuring electrodes within and in a distal position with respect to the stenting balloon.

FIG. 1C illustrates a catheter according to another exemplary embodiment of the present invention having an ultrasound transducer within and in a distal position with respect to the stenting balloon.

FIG. 1D illustrates a catheter according to another exemplary embodiment of the present invention without a stenting balloon.

FIG. 1E illustrates a guide catheter according to another exemplary embodiment of the present invention with wire and impedance electrodes.

FIG. 1F illustrates a catheter according to another exemplary embodiment of the present invention with multiple detection electrodes.

DETAILED DESCRIPTION OF THE INVENTION

Figure 2B:
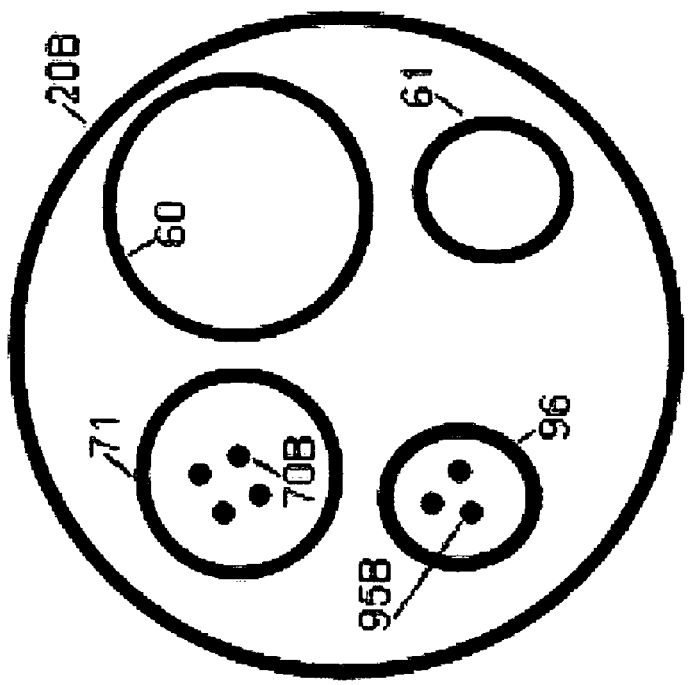
FIG. 2B illustrates a catheter according to another exemplary embodiment of the present invention in cross-section proximal to the location of the sensors showing the leads run in separate lumens.

This invention makes easy, accurate and reproducible measurements of the type or composition of plaques in blood vessels within acceptable limits. This enables the determination of a plaque type and/or composition in order to improve patient health by allowing early treatment options for undersized (but potentially dangerous) plaques that could dislodge and cause infarcts or other health problems.

In the pending parent application, which is incorporated by reference herein in its entirety, a novel technique is introduced that allows the determination of vessel lumen CSA based on an electrical impedance principle. The technique also allows the determination of current loss through the vessel wall, for example, the parallel conductance ($G_p$). Briefly, the methodology involves a multi-injection technique including slightly hypertonic and slightly hypotonic solutions. The two injections with known conductivities allow the measurement of the total conductance for each injection (conductance in the vessel lumen and $G_p$), and hence provide two equations that couple the CSA and $G_p$. Therefore, the CSA and $G_p$ can be determined at any point along the vessel length. An objective of the present invention is to determine the $G_p$ value and determine the plaque type from this value.

$G_p$ is a measure of electrical conductivity through the tissue and is the inverse of electrical resistivity. Fat or lipids have a higher resistivity to electrical flow or a lower $G_p$ than compared to most other issues. For example, lipids have approximately ten times (10×) higher resistivity or ten times (10×) lower conductivity than vascular tissue. In terms of conductivities, fat has a 0.023 S/m value, blood vessel wall has 0.32 S/m, and blood has a 0.7 S/m. Because unstable plaques are characterized by a higher lipid core, a purpose of this invention is to use the value of $G_p$ to identify vulnerable plaque.

Studies indicate that $G_p$ is about 70-80% for a normal vessel (as determined by Equation [6]). This value is significantly reduced when lipid is present in the vessel wall. In other words, the lipid insulates the vessel and significantly reduces the current loss through the wall. The degree of reduction of $G_p$ will be dependent on the fraction of lipid in the plaque. The higher the fraction of lipid, the smaller the value of $G_p$, and consequently the greater the risk of plaque rupture which can cause acute coronary syndrome. Thus, the exemplary embodiments described below and throughout this disclosure are used to develop a measure for the conductance, $G_p$, which in turn is used as a determinant of the type and/or composition of the plaque in the region of measurement.

As described below, in one exemplary embodiment, there is provided an angioplasty catheter with impedance electrodes near the distal end 19 of the catheter (e.g., in front of the balloon) for immediate measurement of the cross-sectional area of a vessel lumen during balloon advancement. This catheter includes electrodes for accurate detection of organ luminal $G_p$ and ports for pressure gradient measurements. Hence, it is not necessary to change catheters such as with the current use of intravascular ultrasound or OCT. In one exemplary embodiment, the catheter provides direct measurement of plaque type (e.g., soft/vulnerable or hard/stable), thereby allowing the selection of an appropriate balloon material (low or high pressure). In another embodiment, additional impedance electrodes may be incorporated in the center of the balloon on the catheter in order to deploy the stent to the desired cross-sectional area. The procedures described herein substantially improve the accuracy of stenting and improve the cost and outcome as well. Furthermore, they allow for proper and accurate assessment of plaque type and/or composition.

Exemplary embodiments of impedance or conductance catheters are illustrated in FIGS. 1A-1F. With reference to the exemplary embodiment shown in FIG. 1A, four wires are threaded through one of two lumens of a 4 Fr catheter. Here, electrodes 26 and 28, are spaced 1 mm apart and form the inner (detection) electrodes. Electrodes 25 and 27 are spaced 4-5 mm from either side of the inner electrodes and form the outer (excitation) electrodes. Such spacing as described herein has been discovered to enhance the excitation and detection functions of the electrodes with respect to the plaque area of interest.

In one approach, dimensions of a catheter to be used for any given application depend on the optimization of the potential field using finite element analysis described below. For small organs or in pediatric patients the diameter of the catheter may be as small as 0.3 mm. In large organs the diameter may be significantly larger depending on the results of the optimization based on finite element analysis. The balloon size will typically be sized according to the exemplary dimension of the organ after the distension. The balloon may be made of materials suitable for the function, such as, for example, polyethylene, latex, polyestherurethane, the like, or combinations thereof. The catheter typically made of PVC or polyethylene, though other materials may equally well be used.

The excitation and detection electrodes typically surround the catheter as ring electrodes but they may also be point electrodes or have other suitable configurations. These electrodes may be made of any conductive material, preferably of platinum iridium or a carbon-coasted surface to avoid fibrin deposits. In the exemplary embodiment, the detection electrodes are spaced with 0.5-1 mm between them and with a distance between 4-5 mm to the excitation electrodes on small catheters. The dimensions of the catheter selected for a treatment depend on the size of the vessel and are preferably determined in part on the results of finite element analysis, described below. On large catheters, for use in larger vessels and other visceral hollow organs, the electrode distances may be larger.

Referring to FIGS. 1A, 1B, 1C and 1D, several embodiments of the catheters are illustrated. The catheters shown contain to a varying degree different electrodes, number and optional balloon(s). With reference to the embodiment shown in FIG. 1A, there is shown an impedance catheter 20 with 4 electrodes 25, 26, 27 and 28 placed close to the tip 19 of the catheter. Proximal to these electrodes is an angiography or stenting balloon 30 capable of being used for treating stenosis. Electrodes 25 and 27 are excitation electrodes, while electrodes 26 and 28 are detection electrodes, which allow measurement of $G_p$ during advancement of the catheter, as described in further detail below. The portion of the catheter 20 within balloon 30 includes an infusion port 35 and a pressure port 36.

The catheter 20 may also advantageously include several miniature pressure transducers (not shown) carried by the catheter or pressure ports for determining the pressure gradient proximal at the site where $G_p$ is measured. The pressure is preferably measured inside the balloon and proximal, distal to and at the location of $G_p$ measurement, and locations proximal and distal thereto, thereby enabling the measurement of pressure recordings at the site of stenosis and also the measurement of pressure-difference along or near the stenosis. In one embodiment, shown in FIG. 1A, catheter 20 advantageously includes pressure port 90 and pressure port 91 proximal to or at the site of $G_p$ for evaluation of pressure gradients. As described below with reference to FIGS. 2A, 2B and 3, in certain embodiments, the pressure ports are connected by respective conduits in the catheter 20 to pressure sensors in the data acquisition system 100 or 300. Such pressure sensors are generally known in the art and include, for example, fiber-optic systems, miniature strain gauges, and perfused low-compliance manometry.

In one embodiment, a fluid-filled silastic pressure-monitoring catheter is connected to a pressure transducer. Luminal pressure can be monitored by a low compliance external pressure transducer coupled to the infusion channel of the catheter. Pressure transducer calibration may be carried out by applying 0 and 100 mmHg of pressure by means of a hydrostatic column.

In one embodiment, shown in FIG. 1B, the catheter 39 includes another set of excitation electrodes 40, 41 and detection electrodes 42, 43 located inside the angioplastic or stenting balloon 30 for accurate determination of the balloon $G_p$ during angioplasty or stent deployment. These electrodes are in addition to electrodes 25, 26, 27 and 28.

In one embodiment, $G_p$ may be measured using a two-electrode system. In another embodiment, illustrated in FIG. 1F, several $G_p$ can be measured using an array of 5 or more electrodes. Here, the excitation electrodes 51, 52, are used to generate the current while detection electrodes 53, 54, 55, 56 and 57 are used to detect the current at their respective sites.

The tip of the catheter can be straight, curved or with an angle to facilitate insertion into the coronary arteries or other lumens. The distance between the balloon and the electrodes is usually small, in the 0.5-2 cm range but can be closer or further away, depending on the particular application or treatment involved.

In another embodiment, shown in FIG. 1C the catheter 21 has one or more imaging or recording device, such as, for example, ultrasound transducers 50 for cross-sectional area and wall thickness measurements. As shown in this embodiment, the transducers 50 are located near the distal tip 19 of the catheter 21.

FIG. 1D illustrates an embodiment of the impedance catheter 22 without an angioplastic or stenting balloon. This catheter also possesses an infusion or injection port 35 located proximal relative to the excitation electrode 25 and pressure port 36.

With reference to the embodiment shown in FIG. 1E, the electrodes 25, 26, 27, 28 can also be built onto a wire 18, such as, for example, a pressure wire, and inserted through a guide catheter 23 where the infusion of bolus can be made through the lumen of the guide catheter 37. The wires are conductively separated from each other to allow for individual recording and relay of values back to the detection system 100 or 300.

With reference to the embodiments shown in FIGS. 1A, 1B, 1C, 1D, 1E and 1F, the impedance catheter advantageously includes optional ports 35, 36, 37 for suction of contents of the organ or infusion of fluid. The suction/infusion port 35, 36, 37 can be placed as shown with the balloon or elsewhere either proximal or distal to the balloon on the catheter. The fluid inside the balloon can be any biologically compatible conducting fluid. The fluid to inject through the infusion port or ports can be any biologically compatible fluid but the conductivity of the fluid is selected to be different from that of blood (e.g., NaCl).

In certain embodiments, the catheter can include a channel 31 for insertion of a guide wire to stiffen the flexible catheter during the insertion or data recording. Additionally, the same channel 31 may be used to inject fluid solutions of various concentrations into the plaque area of interest. An additional channel 32 may be connected to the catheter such that the electrical wires connected to the one or more electrodes on the catheter are directed through the additional channel 32 and to an assessment system, such as 100 or 300, through an adaptor interface 33, such as an impedance module plug or the like, as described in more detail below.

Figure 8:
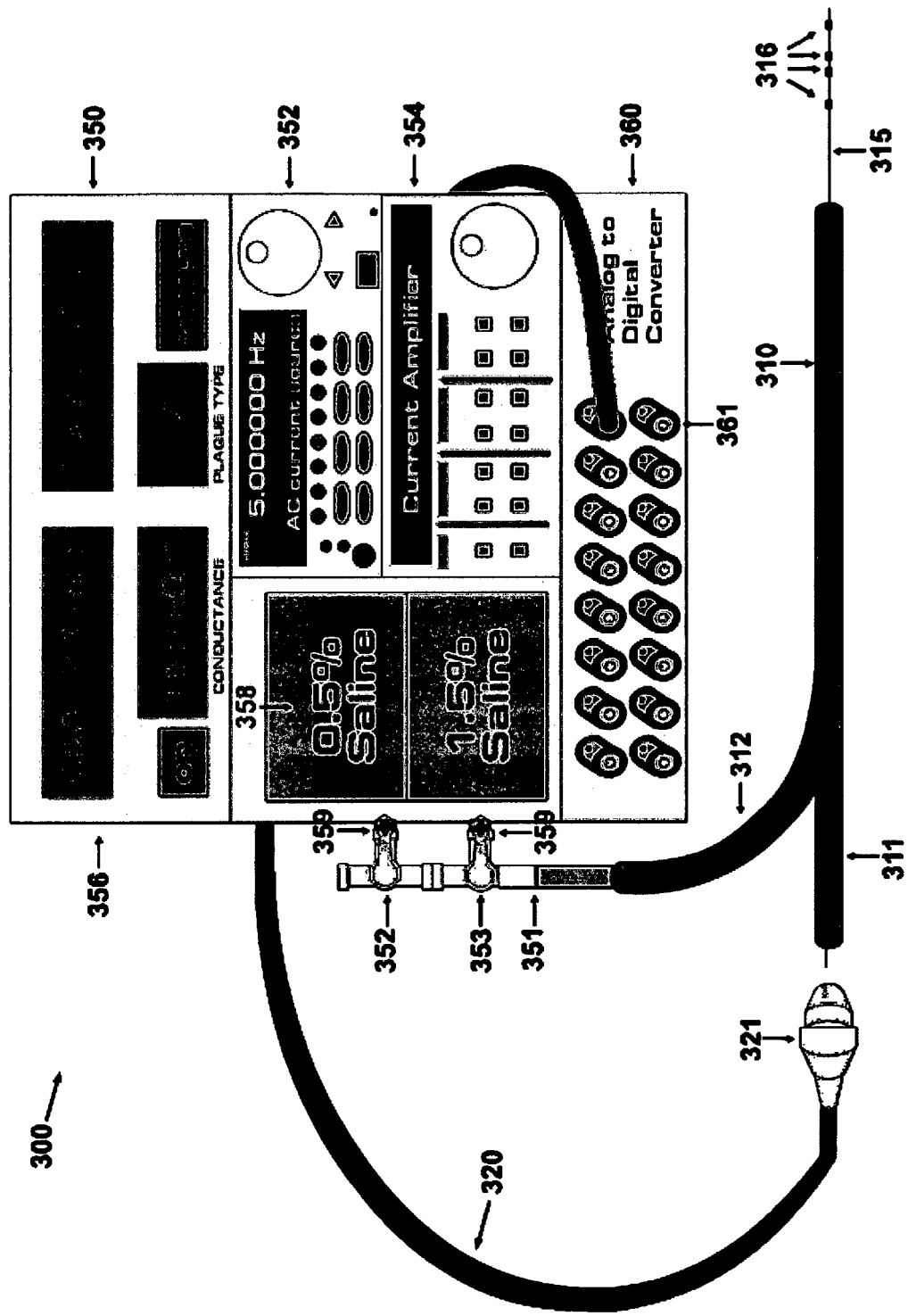
FIG. 8 shows an exemplary assessing system according to the present invention that measures and detects the cross sectional area and/or conductance of a plaque area.

In some embodiments, such as depicted in FIG. 1E, an adaptor interface 33 may be used to house and guide the electrical wires back to a system 100 or 300 while a side channel 34 is used to inject fluids of varying concentrations into the catheter 23. An illustration of a catheter system 300 using a catheter such as the one shown in FIG. 1E is shown in FIG. 8 and described in more detail below. Such fluid used herein may be, for example, solutions at various concentrations used to determine cross sectional area and/or conductance. In yet another embodiment (not illustrated), the catheter includes a sensor for measurement of the flow of fluid in the body organ.

Systems for Determining $G_p$ and Pressure Gradient

The operation of the impedance catheter 20 is as follows: With reference to the embodiment shown in FIG. 1A for electrodes 25, 26, 27, 28, conductance of current flow through the vessel lumen and vessel wall and surrounding tissue is parallel; e.g., $$G(z, t) = \frac{CSA(z, t) \cdot C_b}{L} + G_p(z, t) \tag{1a}$$

where $G_p(z,t)$ is the effective conductance of the structure outside the bodily fluid (vessel wall and surrounding tissue); $C_b$ is the specific electrical conductivity of the bodily fluid, which for blood generally depends on the temperature, hematocrit and orientation and deformation of blood cells; and L is the distance between the detection electrodes. Equation [1a] can be rearranged to solve for cross sectional area $CSA(z,t)$, with a correction factor, $\alpha$, if the electric field is non-homogeneous, as $$CSA(z, t) = \frac{L}{\alpha C_b}[G(z, t) - G_p(z, t)] \tag{1b}$$

where $\alpha$ would be equal to 1 if the field were completely homogeneous. The parallel conductance, $G_p$, is an offset error that results from current leakage. $G_p$ would equal 0 if all of the current were confined to the blood (e.g., insulated) and hence would correspond to the cylindrical model given by Equation [10]. In one approach, finite element analysis is used to properly design the spacing between detection and excitation electrodes relative to the dimensions of the vessel to provide a nearly homogenous field such that a can be considered equal to 1. Simulations show that a homogenous or substantially homogenous field is provided by (1) the placement of detection electrodes substantially equidistant from the excitation electrodes and (2) maintaining the distance between the detection and excitation electrodes substantially comparable to the vessel diameter. In one approach, a homogeneous field is achieved by taking steps (1) and/or (2) described above so that a equals 1 in the foregoing analysis.

At any given position, z, along the long axis of organ and at any given time, t, in the cardiac cycle, $G_p$ is a constant. Hence, two injections of different concentration of NaCl solution give rise to two equations:

$$C_1 \cdot CSA(z,t) + L \cdot G_p(z,t) = L \cdot G_1(z,t) \tag{2}$$

and $$C_2 \cdot CSA(z,t) + L \cdot G_p(z,t) = L \cdot G_2(z,t) \tag{3}$$

which can be solved simultaneously for CSA and $G_p$ as $$CSA(z, t) = L\frac{[G_2(z, t) - G_1(z, t)]}{[C_2 - C_1]} \tag{4}$$

and $$G_p(z, t) = \frac{[C_2 \cdot G_1(z, t) - C_1 \cdot G_2(z, t)]}{[C_2 - C_1]} \tag{5}$$

where subscript "1" and subscript "2" designate any two injections of different NaCl concentrations. For each injection k, $C_k$ gives rise to $G_k$, which is measured as the ratio of the root mean square of the current divided by the root mean square of the voltage. The $C_k$ is typically determined through in vitro calibration for the various NaCl concentrations. The concentration of NaCl used is typically on the order of 0.45 to 1.8%. The volume of NaCl solution is typically about 5 ml, but sufficient to displace the entire local vascular blood volume momentarily. The value of $G_p$(t) can be determined at end-diastole or end-systole (e.g., the minimum and maximum values) or the mean thereof. The value of CSA would vary through the cycle but $G_p$ does not vary significantly.

It is apparent that the total conductance is the sum of the conductance in the vessel lumen and the conductance through the vessel wall and surrounding tissue (current "leakage") as expressed by Equation [1a]. In order to assess the contribution of the current "leakage" or $G_p$, we can evaluate the contribution of $G_p$ to the total conductance as follows:

$$\% G_p = \frac{G_p}{\left[\frac{G_{0.5\% \ NaCl} + G_{1.5\% \ NaCl}}{2}\right]} \times 100 \tag{6}$$

where the total conductance on the denominator is taken as the average of the total conductance of the two injections.

In one approach, a pull or push through is used to reconstruct the $G_p$ along its vessel length. During a long injection (e.g., 10-15 s), the catheter can be pulled back or pushed forward at constant velocity U. Equation [1a] can be expressed as $$G(U \cdot t, t) = \frac{CSA(U \cdot t, t) \cdot C_b}{L} + G_p(U \cdot t, t) \tag{7}$$

where the axial position, z, is the product of catheter velocity, U, and time, t; i.e., z=U·t.

For the two injections, denoted by subscript "1" and subscript "2", respectively, we can consider different time points $T_1$, $T_2$, etc. such that equation [7] can be written as $$G_1(U \cdot T_1, t) = \frac{CSA_1(U \cdot T_1, t) \cdot C_1}{L} + G_{p_1}(U \cdot T_1, t) \quad [8a]$$

$$G_2(U \cdot T_1, t) = \frac{CSA_1(U \cdot T_1, t) \cdot C_2}{L} + G_{p_1}(U \cdot T_1, t) \quad [8b]$$

and $$G_1(U \cdot T_2, t) = \frac{CSA_2(U \cdot T_2, t) \cdot C_1}{L} + G_{p2}(U \cdot T_2, t) \quad [9a]$$

$$G_2(U \cdot T_2, t) = \frac{CSA_2(U \cdot T_2, t) \cdot C_2}{L} + G_{p2}(U \cdot T_2, t) \quad [9b]$$

and so on. Each set of equations [8a], [8b] and [9a], [9b], etc. can be solved for $CSA_1$, $G_{p1}$ and $CSA_2$, $G_{p2}$, respectively. Hence, we can measure the $G_p$ at various time intervals and hence at different positions along the vessel to reconstruct the length of the vessel.

In an exemplary embodiment, the data on parallel conductance as a function of longitudinal position along the vessel can be exported from an electronic spreadsheet, such as, for example, a Microsoft Excel file, to a diagramming software, such as AutoCAD, where the software uses the coordinates to render the axial variation of $G_p$ score (% $G_p$).

Furthermore, the $G_p$ score may be scaled through a scaling model index to simplify its relay of information to a user. An example of a scaling index used in the present invention is to designate a single digit whole number to represent the calculated conductance $G_p$ as determined by Equation [6]. In such a scaling index, "0" would designated a calculated $G_p$ of 0-9%; "1" would designate a calculated $G_p$ of 10-19%; "2" would designate a calculated $G_p$ of 20-29%; . . . ; and "9" would designate a calculated $G_p$ of 90-100%. In this scaling index example, a designation of 0, 1, 2, 3, 4, 5 or 6 would represent a risky plaque composition, with the level of risk decreasing as the scaling number increases, because the generally low level of conductance meaning generally higher fat or lipid concentrations. In contrast, a designation of 7, 8 or 9 would generally represent a non-risky plaque composition, with the level of risk decreasing as the scaling number increases, because the generally higher level of conductance meaning generally lower fat or lipid concentrations. An example of use of this scaling index is shown in the visual display area of system 300 shown in FIG. 8.

In one exemplary approach, the pull back reconstruction was made during a long injection where the catheter was pulled back at constant rate by hand. The catheter was marked along its length such that the pull back was made at 2 mm/sec. Hence, during a 10 second injection, the catheter was pulled back about 2 cm. The data was continuously measured and analyzed at every two second interval; i.e., at every 4 mm. Hence, six different measurements of CSA and $G_p$ were made which were used to reconstruction the CSA and $G_p$ along the length of the 2 cm segment.

Operation of the impedance catheter 39: With reference to the embodiment shown in FIG. 1B, the voltage difference between the detection electrodes 42 and 43 depends on the magnitude of the current (I) multiplied by the distance (L) between the detection electrodes and divided by the conductivity (C) of the fluid and the cross-sectional area (CSA) of the artery or other organs into which the catheter is introduced. Since the current (I), the distance (L) and the conductivity (C) normally can be regarded as calibration constants, an inverse relationship exists between the voltage difference and the CSA as shown by the following equations:

$$G = \frac{C \cdot CSA}{L} \quad [10]$$

where G is conductance expressed as the ratio of current to voltage (I/ΔV). Equation [10] is identical to equation [1b] if we neglect the parallel conductance through the vessel wall and surrounding tissue because the balloon material acts as an insulator. This is the cylindrical model on which the conductance method is used.

As described below with reference to FIGS. 2A, 2B, 3, 4 and 5, the excitation and detection electrodes are electrically connected to electrically conductive leads in the catheter for connecting the electrodes to the data acquisition system 100 or 300.

Figure 2A:
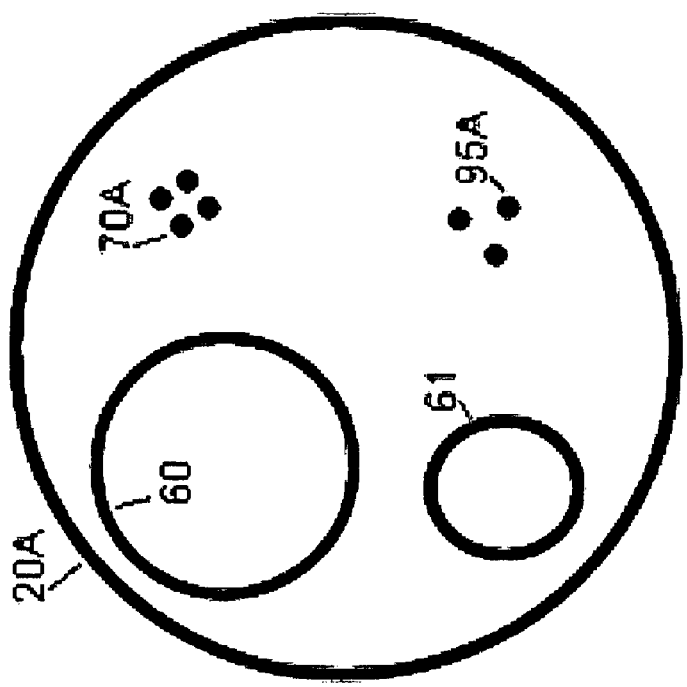
FIG. 2A illustrates a catheter according to an exemplary embodiment of the present invention in cross-section proximal to the location of the sensors showing the leads embedded in the material of the probe.

FIGS. 2A and 2B illustrate two embodiments 20A and 20B of an exemplary catheter as shown in any of FIGS. 1A-1F in cross-section. Each embodiment has a lumen 60 for inflating and deflating the balloon and a lumen 61 for suction and infusion. The sizes of these lumens can vary in size. The impedance electrode electrical leads 70A are embedded in the material of the catheter in the embodiment in FIG. 2A, whereas the electrode electrical leads 70B are tunneled through a lumen 71 formed within the body of catheter 70B in FIG. 2B.

Pressure conduits for perfusion manometry connect the pressure ports 90, 91 to transducers included in the data acquisition system 100. As shown in FIG. 2A pressure conduits 95A may be formed in 20A. In another embodiment, shown in FIG. 2B, pressure conduits 95B constitute individual conduits within a tunnel 96 formed in catheter 20B. In the embodiment described above where miniature pressure transducers are carried by the catheter, electrical conductors will be substituted for these pressure conduits.

Figure 3:
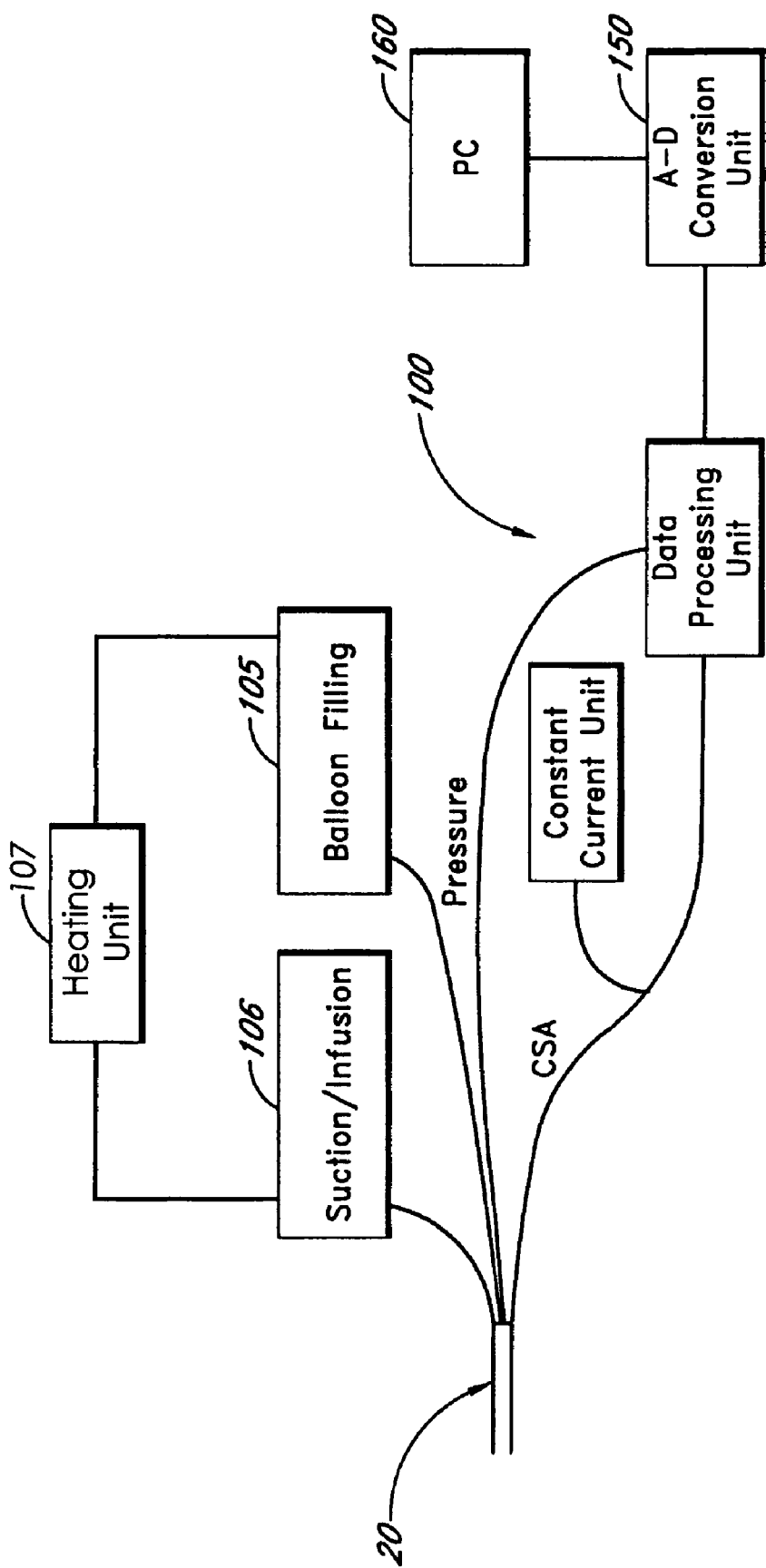
FIG. 3 is a schematic of a system according to an exemplary embodiment of the present invention showing a catheter carrying impedance measuring electrodes connected to the data acquisition equipment and excitation unit for the cross-sectional area measurement.

With reference to FIG. 3, in one embodiment, the catheter 20 connects to a data acquisition system 100, to a manual or automatic system 105 for distension of the balloon and to a system 106 for infusion of fluid or suction of blood. The fluid is heated to 37-39° or equivalent to body temperature with heating unit 107. The impedance planimetry system typically includes a constant current unit, amplifiers and signal conditioners. The pressure system typically includes amplifiers and signal conditioners. The system can optionally contain signal conditioning equipment for recording of fluid flow in the organ.

In one exemplary embodiment, the system is pre-calibrated and the probe is available in a package. Here, the package also preferably contains sterile syringes with the fluids to be injected. The syringes are attached to the machine and after heating of the fluid by the machine and placement of the probe in the organ of interest, the user presses a button that initiates the injection with subsequent computation of the desired parameters. $G_p$ and other relevant measures such as distensibility, tension, etc., will typically appear on the display panel in the PC module 160. Here, the user can then remove the stenosis by distension or by placement of a stent. The value of $G_p$, which reflects the "hardness" (high $G_p$) or "softness" (low $G_p$), can be used in selection of high or low pressure balloons as known in the arts.

The embodiment shown in FIG. 8 presents an example of what an overall system 300 may look like in terms of various components and optional elements. As shown in the figure, system 300 includes a control device 350, a catheter 310 and an electrical connecting tube 320. Control device 350 allows control of numerous variables through control gauges for current 352, current amplification 354, analog to digital (A/D) conversion 360 and various solution concentrations 358. Solutions at varying concentrations may be held in one or more containers attached or controlled by the solution-controlling segment 358 of control device 350. For example, such solutions may be pre-made and pre-deposited into control device 350 before the start of plaque determination analysis.

Each solution at a different concentration may be individually connected to a solution-receiving channel 312 of a catheter 310 through a solution port 351. For example, a 0.5% saline solution is connected to solution port 351 through container port 359 connected to spigot 352. A similar set up connects a 1.5% saline solution to the solution-receiving channel 312 of catheter 310 through container port 359 connected to spigot 353 flowing to solution port 351. Spigot 352 may be opened to allow the 0.5% solution flow through to the catheter while spigot 353 is closed to the flow of the 1.5% solution, and vice versa. This allows for easy and sequential control of fluid injection of various concentrations into catheter 310 without mixing, which then directs such specific concentration fluid to a plaque site as described elsewhere in this disclosure.

Furthermore, a wire 315 having one or more electrodes 316 thereon and made available to a plaque site, as described elsewhere in this disclosure, is connected to an electrical adaptor 321 that links the wire 315 to an electrical connecting tube 320 back to the control device 350 through the A/D converter area 360. One or more A/D converter connections 361 may be made available on the control device 350 to measure one or more electrical activity for one or more catheters. Thus, a multi-catheter study of multiple plaque sites may be made using a single control device 350.

All measurement and analysis results may be shown on a single display panel 356. Variables that are calculated by the internal computer using the formulas and finite element analysis described in this disclosure are displayed in real time in the display panel area 356. Exemplary display results include, but are not limited to, the cross-sectional area of the measurement sight, the temperature, the conductance value (total and/or parallel) and even a resultant determination of the plaque type by a pre-set range of conductance values that pre-classify certain plaque types, as set forth by the exemplary scaling model described above.

For example, for a given determination of a conductance value of 68% (as determined by the internal computer using equation [6]), the resultant plaque type would be deemed as "6" or somewhat fatty. This would be a simple automated analysis of the plaque site under consideration based on the teachings and discoveries of the present invention as described throughout this disclosure. Of course, the range for the scaling model described above could be pre-set by the manufacturer according to established studies, but may be later changed by the individual clinic or user based on further or subsequent studies.

In use, system 300 gives the user a simple, effective and powerful tool to relay information about a vessel site and any plaque housed therein. A user would first consider the CSA level as the catheter is pulled through the site or as numerous electrodes calculate the CSA as their designated cross-sectional place, as described elsewhere in this disclosure. If there is little to no changes in the CSA value, then the user would acknowledge that there is little to no obstructions or plaques within the lumen of the blood vessel. However, if there is some change in the value of the CSA, then the conductance measurement and plaque type information is monitored to determine the extent to which plaque formation is present as well as the type of plaque, as determined by the scaling model whole number displayed, as described above.

In one embodiment, the impedance and pressure data are analog signals, which are converted by analog-to-digital converters 150 and transmitted to a computer 160 for on-line display, on-line analysis and storage. In another embodiment, all data handling is done on an entirely analog basis. The analysis advantageously includes software programs for reducing the error due to conductance of current in the organ wall and surrounding tissue and for displaying the $G_p$ distribution along the length of the vessel along with the pressure gradient. In one embodiment of the software, a finite element approach or a finite difference approach is used to derive the $G_p$ of the organ stenosis taking parameters such as conductivities of the fluid in the organ and of the organ wall and surrounding tissue into consideration. In another embodiment, simpler circuits are used; e.g., based on making two or more injections of different NaCl solutions to vary the resistivity of fluid in the vessel and solving the two simultaneous equations [2] and [3] for the $G_p$ (equations [4] and [5], respectively). In another embodiment, the software contains the code for reducing the error in luminal $G_p$ measurement by analyzing signals during interventions such as infusion of a fluid into the organ or by changing the amplitude or frequency of the current from the constant current amplifier. The software chosen for a particular application preferably allows computation of $G_p$ with only a small error instantly or within acceptable time during the medical procedure.

In one approach, the wall thickness is determined from the parallel conductance for those organs that are surrounded by air or non-conducting tissue. In such cases, the parallel conductance is equal to $$G_p = \frac{CSA_w \cdot C_w}{L} \qquad [11a]$$

where $CSA_w$ is the wall area of the organ and $C_w$ is the electrical conductivity through the wall. This equation can be solved for the wall $CSA_w$ as $$CSA_w = \frac{G_p \cdot L}{C_w} \qquad [11b]$$

For a cylindrical organ, the wall thickness, h, can be expressed as $$h = \frac{CSA_w}{\pi D} \qquad [12]$$

where D is the diameter of the vessel, which can be determined from the circular CSA ($D=[4CSA/\pi]^{1/2}$).

When the CSA, pressure, wall thickness, and flow data are determined according to the embodiments outlined above, it is possible to compute the compliance (e.g., $\Delta CSA/\Delta P$), tension (e.g., $P*r$, where P and r are the intraluminal pressure and radius of a cylindrical organ), stress (e.g., $P*r/h$ where h is the wall thickness of the cylindrical organ), strain (e.g., $(C-C_d)/C_d$ where C is the inner circumference and $C_d$ is the circumference in diastole) and wall shear stress (e.g., $4 \mu Q/r^3$ where $\mu$, Q and r are the fluid viscosity, flow rate and radius of the cylindrical organ, respectively, for a fully developed flow).

These quantities can be used in assessing the mechanical characteristics of the system in health and disease.

To consider a method of measuring $G_p$ and related impedance, which are used to evaluate the type and/or composition of a plaque, a number of approaches may be used. In one approach, $G_p$ is measured by introducing a catheter from an exteriorly accessible opening into the hollow system or targeted luminal organ. For cardiovascular applications, the catheter can be inserted into the organs in various ways; e.g., similar to conventional angioplasty. In one embodiment, an 18 gauge needle is inserted into the femoral artery followed by an introducer. A guide wire is then inserted into the introducer and advanced into the lumen of the femoral artery. A 4 or 5 Fr conductance catheter is then inserted into the femoral artery via wire and the wire is subsequently retracted. The catheter tip containing the conductance electrodes can then be advanced to the region of interest by use of x-ray (e.g., fluoroscopy). In another approach, this methodology is used on small to medium size vessels (e.g., femoral, coronary, carotid, iliac arteries, etc.).

In another approach, a minimum of two injections (with different concentrations of NaCl) is required to solve for $G_p$. In yet another approach, three injections will yield three sets of values for CSA and $G_p$ (although not necessarily linearly independent), while four injections would yield six sets of values. In one approach, at least two solutions (e.g., 0.5% and 1.5% NaCl solutions) are injected in the targeted luminal organ or vessel. Studies indicate that an infusion rate of approximately 1 ml/s for a five second interval is sufficient to displace the blood volume and results in a local pressure increase of less than 10 mmHg in the coronary artery. This pressure change depends on the injection rate, which should be comparable to the organ flow rate.

In one exemplary approach, involving the application of Equations [4] and [5], the vessel is under identical or very similar conditions during the two injections. Hence, variables, such as, for example, the infusion rate, bolus temperature, etc., are similar for the two injections. Typically, a short time interval is to be allowed (1-2 minute period) between the two injections to permit the vessel to return to homeostatic state. This can be determined from the baseline conductance as shown in FIG. 4 or 5. The parallel conductance is preferably the same or very similar during the two injections. In one approach, dextran, albumin or another large molecular weight molecule can be added to the NaCl solutions to maintain the colloid osmotic pressure of the solution to reduce or prevent fluid or ion exchange through the vessel wall.

In one approach, the NaCl solution is heated to body temperature prior to injection since the conductivity of current is temperature dependent. In another approach, the injected bolus is at room temperature, but a temperature correction is made since the conductivity is related to temperature in a linear fashion.

In one approach, a sheath is inserted either through the femoral or carotid artery in the direction of flow. To access the left anterior descending (LAD) artery, the sheath is inserted through the ascending aorta. For the carotid artery, where the diameter is typically on the order of 5-5.5 mm, a catheter having a diameter of 1.9 mm can be used, as determined from finite element analysis, discussed further below. For the femoral and coronary arteries, where the diameter is typically in the range from 3.5-4 mm, so a catheter of about 0.8 mm diameter would be appropriate. The catheter can be inserted into the femoral, carotid or LAD artery through a sheath appropriate for the particular treatment. Measurements for all three vessels can be made similarly.

To validate the measurement of $G_p$ with the measurement of CSA, the protocol and results are described here for one exemplary approach that is generally applicable to most arterial vessels. The conductance catheter was inserted through the sheath for a particular vessel of interest. A baseline reading of voltage was continuously recorded. Two containers containing 0.5% and 1.5% NaCl were placed in temperature bath and maintained at 37°. A 5-10 ml injection of 1.5% NaCl was made over a 5 second interval. The detection voltage was continuously recorded over a 10 second interval during the 5 second injection. Several minutes later, a similar volume of 1.5% NaCl solution was injected at a similar rate. The data was again recorded. Matlab was used to analyze the data including filtering with high pass and with low cut off frequency (1200 Hz). The data was displayed using Matlab and the mean of the voltage signal during the passage of each respective solution was recorded. The corresponding currents were also measured to yield the conductance (G=I/V). The conductivity of each solution was calibrated with six different tubes of known CSA at body temperature. A model using equation [10] was fitted to the data to calculate conductivity C. The analysis was carried out in SPSS using the non-linear regression fit. Given C and G for each of the two injections, an excel sheet file was formatted to calculate the CSA and $G_p$ as per equations [4] and [5], respectively. These measurements were repeated several times to determine the reproducibility of the technique. The reproducibility of the data was within 5%. Ultrasound (US) was used to measure the diameter of the vessel simultaneous with our conductance measurements. The detection electrodes were visualized with US and the diameter measurements was made at the center of the detection electrodes. The maximum differences between the conductance and US measurements were within 10%.

FIGS. 4A, 4B, 5A and 5B illustrate voltage measurements in the blood stream in the left carotid artery. Here, the data acquisition had a sampling frequency of 75 KHz, with two channels—the current injected and the detected voltage, respectively. The current injected has a frequency of 5 KHz, so the voltage detected, modulated in amplitude by the impedance changing through the bolus injection will have a spectrum in the vicinity of 5 KHz.

Figure 4A:
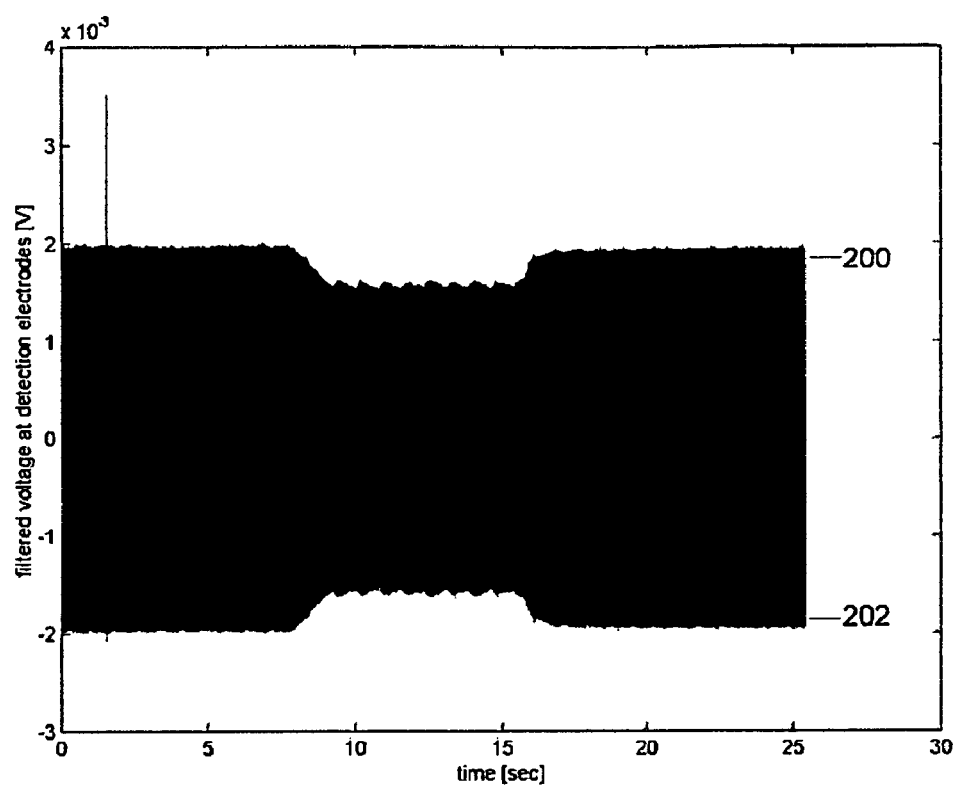
FIG. 4A shows an example of the detected filtered voltage drop as measured in the blood stream before and after injection of 1.5% NaCl solution.
Figure 4B:
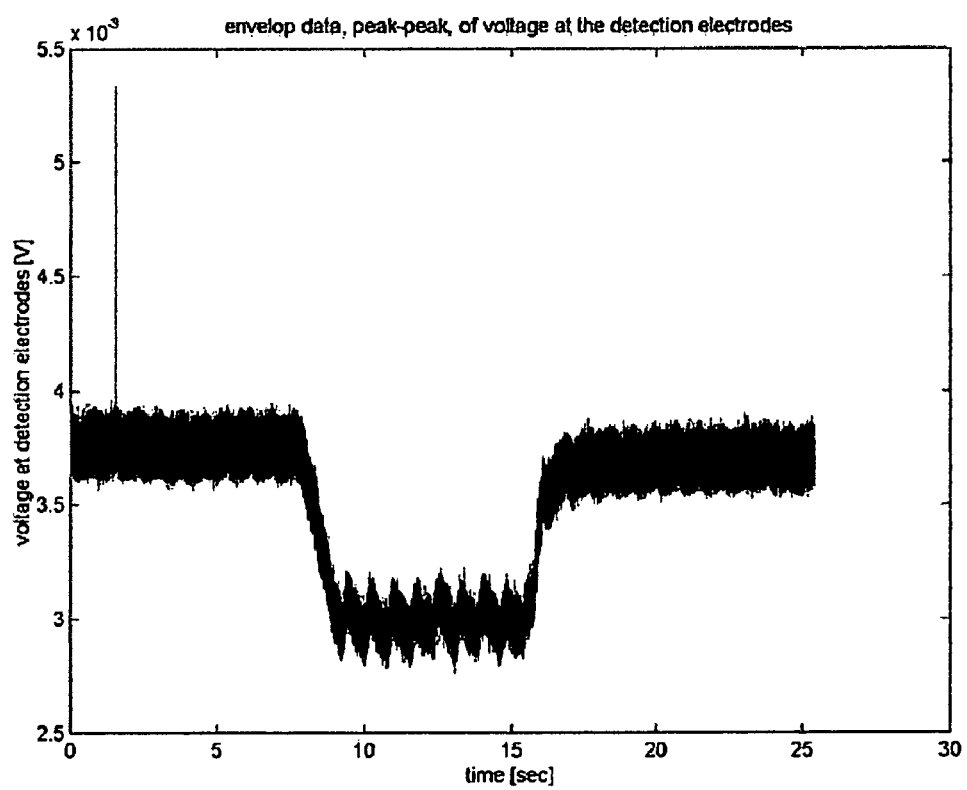
FIG. 4B shows an example of the peak-to-peak envelope of the detected voltage shown in FIG. 4A.
Figure 5A:
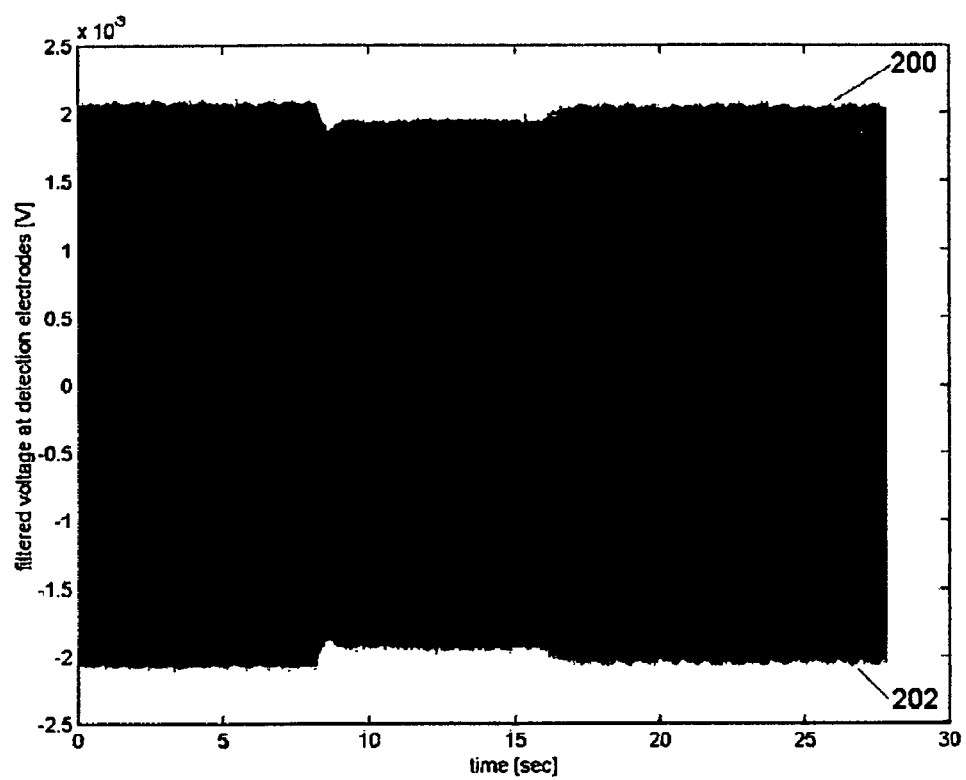
FIG. 5A shows an example of the detected filtered voltage drop as measured in the blood stream before and after injection of 0.5% NaCl solution.
Figure 5B:
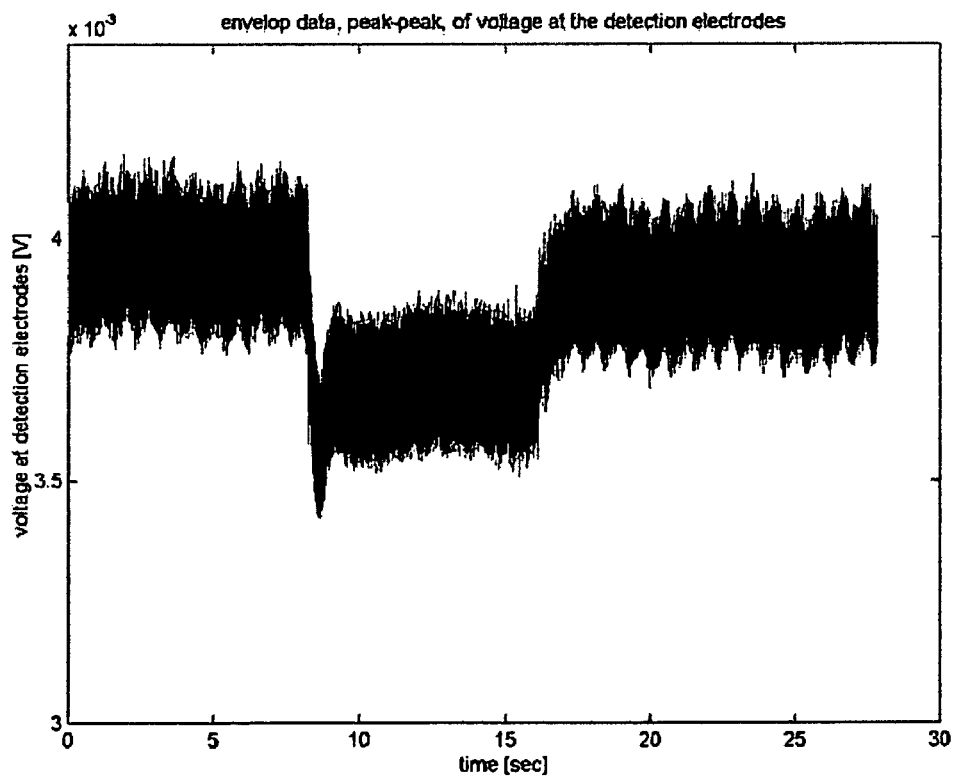
FIG. 5B shows an example of the peak-to-peak envelope of the detected voltage shown in FIG. 5A.

With reference to FIG. 4A there is shown a signal processed with a high pass filter with low cut off frequency (1200 Hz). The top and bottom portions 200, 202 show the peak-to-peak envelope detected voltage which is displayed in FIG. 4B (bottom). The initial 7 seconds correspond to the baseline; i.e., electrodes in the blood stream. The next 7 seconds correspond to an injection of hyper-osmotic NaCl solution (1.5% NaCl). It can be seen that the voltage is decreased implying increase conductance (since the injected current is constant). Once the NaCl solution is washed out, the baseline is recovered as can be seen in the last portion of the FIGS. 4A and 4B. FIGS. 5A and 5B shows similar data corresponding to 0.5% NaCl solutions.

The voltage signals are ideal since the difference between the baseline and the injected solution is apparent and systematic. Furthermore, the pulsation of vessel diameter can be seen in the 0.5% and 1.5% NaCl injections (FIGS. 4 and 5, respectively).

The NaCl solution can be injected by hand or by using a mechanical injector to momentarily displace the entire volume of blood or bodily fluid in the vessel segment of interest. The pressure generated by the injection will not only displace the blood in the antegrade direction (in the direction of blood flow) but also in the retrograde direction (momentarily push the blood backwards). In other visceral organs that may be normally collapsed, the NaCl solution will not displace blood as in the vessels but will merely open the organs and create a flow of the fluid. In one approach, after injection of a first solution into the treatment or measurement site, sensors monitor and confirm baseline of conductance prior to injection of a second solution into the treatment site.

The injections described above are preferably repeated at least once to reduce errors associated with the administration of the injections, such as, for example, where the injection does not completely displace the blood or where there is significant mixing with blood. It will be understood that any bifurcation(s) (with branching angle near 90 degrees) near the targeted luminal organ can cause an error in the calculated $G_p$. Hence, generally the catheter should be slightly retracted or advanced and the measurement repeated. An additional application with multiple detection electrodes or a pull back or push forward during injection will accomplish the same goal. Here, an array of detection electrodes can be used to minimize or eliminate errors that would result from bifurcations or branching in the measurement or treatment site.

In one approach, error due to the eccentric position of the electrode or other imaging device can be reduced by inflation of a balloon on the catheter. The inflation of balloon during measurement will place the electrodes or other imaging device in the center of the vessel away from the wall. In the case of impedance electrodes, the inflation of balloon can be synchronized with the injection of bolus where the balloon inflation would immediately precede the bolus injection. Our results, however, show that the error due to catheter eccentricity is small.

The signals are generally non-stationary, nonlinear and stochastic. To deal with non-stationary stochastic functions, one can use a number of methods, such as the Spectrogram, the Wavelet's analysis, the Wigner-Ville distribution, the Evolutionary Spectrum, Modal analysis, or preferably the intrinsic model function (IMF) method. The mean or peak-to-peak values can be systematically determined by the aforementioned signal analysis and used in Equation [4] to compute the $G_p$.

Figure 6:
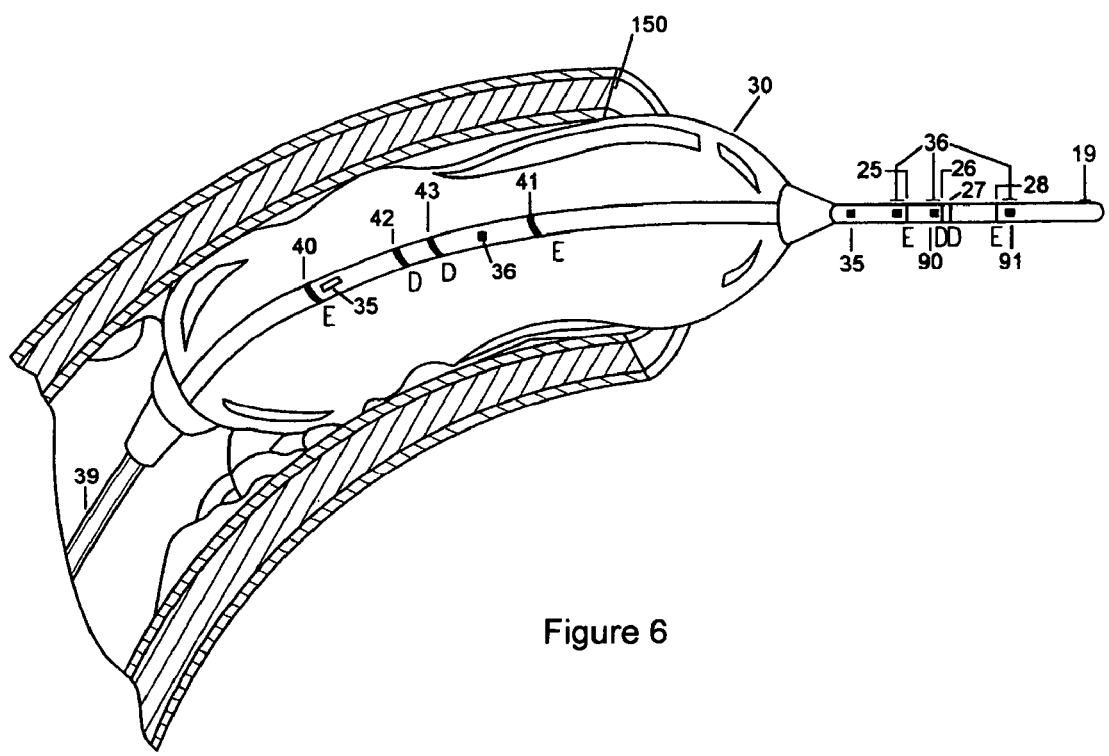
FIG. 6 shows a balloon distension of the lumen of the coronary artery according to an exemplary embodiment of the present invention.
Figure 7:
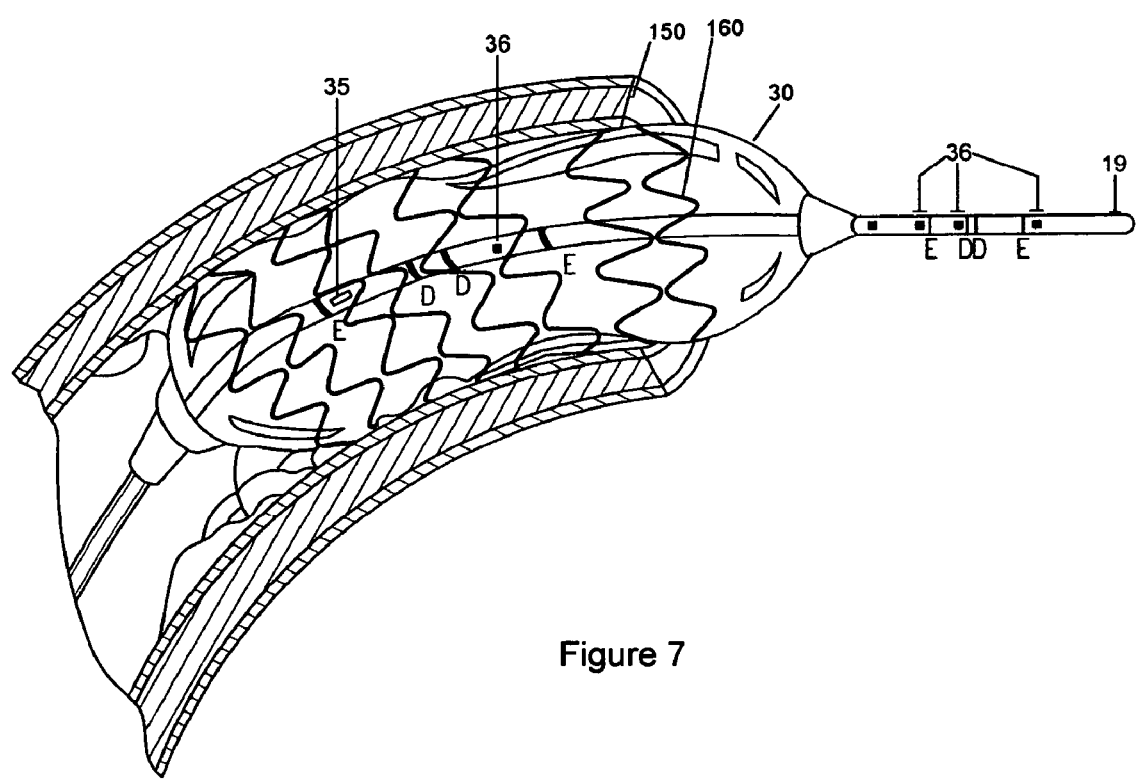
FIG. 7 shows a balloon distension of a stent into the lumen of the coronary artery according to another exemplary embodiment of the present invention.

Referring to the embodiment shown in FIG. 6, the angioplasty balloon 30 is selected on the basis of $G_p$ and is shown distended within the coronary artery 150 for the treatment of stenosis. As described above with reference to FIG. 1B, a set of excitation electrodes 40, 41 and detection electrodes 42, 43 are located within the angioplasty balloon 30. In another embodiment, shown in FIG. 7, the angioplasty balloon 30 is used to distend the stent 160 within blood vessel 150.

In one approach, concomitant with measuring $G_p$ and or pressure gradient at the treatment or measurement site, a mechanical stimulus is introduced by way of inflating a low or high pressure balloon based on high or low value of $G_p$, respectively. This releases stent from the catheter, thereby facilitating flow through the stenosed part of the organ. In another approach, concomitant with measuring $G_p$ and or pressure gradient at the treatment site, one or more pharmaceutical substances for diagnosis or treatment of stenosis is injected into the treatment site. For example, in one approach, the injected substance can be smooth muscle agonist or antagonist. In yet another approach, concomitant with measuring $G_p$ and or pressure gradient at the treatment site, an inflating fluid is released into the treatment site for release of any stenosis or materials causing stenosis in the organ or treatment site.

Again, it will be noted that the methods, systems, and catheters described herein can be applied to any body lumen or treatment site. For example, the methods, systems, and catheters described herein can be applied to any one of the following exemplary bodily hollow systems: the cardiovascular system including the heart; the digestive system; the respiratory system; the reproductive system; and the urogenital tract.

Finite Element Analysis: In one exemplary approach, finite element analysis (FEA) is used to verify the validity of Equations [4] and [5]. There are two major considerations for the model definition: geometry and electrical properties. The general equation governing the electric scalar potential distribution, V, is given by Poisson's equation as:

$$\nabla \cdot (C \nabla V) = -I \quad [13]$$

where C, I and $\nabla$ are the conductivity, the driving current density and the del operator, respectively. Femlab or any standard finite element packages can be used to compute the nodal voltages using equation [13]. Once V has been determined, the electric field can be obtained from as $E = -\nabla V$.

The FEA allows the determination of the nature of the field and its alteration in response to different electrode distances, distances between driving electrodes, wall thicknesses and wall conductivities. The percentage of total current in the lumen of the vessel (% I) can be used as an index of both leakage and field homogeneity. Hence, the various geometric and electrical material properties can be varied to obtain the optimum design; e.g., minimize the non-homogeneity of the field. Furthermore, we simulated the experimental procedure by injection of the two solutions of NaCl to verify the accuracy of equation [4]. Finally, we assessed the effect of presence of electrodes and catheter in the lumen of vessel. The error terms representing the changes in measured conductance due to the attraction of the field to the electrodes and the repulsion of the field from the resistive catheter body were quantified.

The Poisson's equation was solved for the potential field, which takes into account the magnitude of the applied current, the location of the current driving and detection electrodes, and the conductivities and geometrical shapes in the model including the vessel wall and surrounding tissue. This analysis suggest that the following conditions are optimal for the cylindrical model: (1) the placement of detection electrodes equidistant from the excitation electrodes; (2) the distance between the current driving electrodes should be much greater than the distance between the voltage sensing electrodes; and (3) the distance between the detection and excitation electrodes is comparable to the vessel diameter or the diameter of the vessel is small relative to the distance between the driving electrodes. If these conditions are satisfied, the equipotential contours more closely resemble straight lines perpendicular to the axis of the catheter and the voltage drop measured at the wall will be nearly identical to that at the center. Since the curvature of the equipotential contours is inversely related to the homogeneity of the electric field, it is possible to optimize the design to minimize the curvature of the field lines. Consequently, in one exemplary approach, one or more of conditions (1)-(3) described above are met to increase the accuracy of the cylindrical model.

The foregoing disclosure of the exemplary embodiments of the present invention has been presented for purposes of illustration and description. It is not intended to be exhaustive or to limit the invention to the precise forms disclosed. Many variations and modifications of the embodiments described herein will be apparent to one of ordinary skill in the art in light of the above disclosure. The scope of the invention is to be defined only by the claims appended hereto, and by their equivalents.

Further, in describing representative embodiments of the present invention, the specification may have presented the method and/or process of the present invention as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process of the present invention should not be limited to the performance of their steps in the order written, and one skilled in the art can readily appreciate that the sequences may be varied and still remain within the spirit and scope of the present invention.

What is claimed is:

1. A device for assessing composition of a plaque, the device comprising:
   an elongated body having a lumen therethrough along a longitudinal length of the elongated body;
   a pair of excitation electrodes located on the elongated body; and
   a pair of detection electrodes located in between the pair of excitation electrodes;
   the at least one excitation electrode in communication with a current source, the current source operable to supply electrical current to the plaque at the plaque site to allow measurement of two or more conductance values at the plaque site by the detection electrodes, resulting in a determination of the plaque as being at least partially fatty if the value of % $G_p$ as determined by $$\% G_p = \frac{G_p}{\left[\frac{G_{0.5\%NaCl} + G_{1.5\%NaCl}}{2}\right]} \times 100$$

is less than 70%.

2. A method for measuring the composition of a plaque, the method comprising:
   introducing a catheter into the plaque site;
   injecting a first solution of a first compound having a first concentration into the treatment site;
   measuring a first conductance value at the plaque site;
   injecting a second solution of a second compound having a different concentration into the plaque site;
   measuring a second conductance value at the plaque site; and
   determining the composition of the plaque based on the first and second conductance values and the conductivity values of the first and second compounds;
   wherein a plaque is deemed as partially fatty if the value of % $G_p$ as determined by $$\% G_p = \frac{G_p}{\left[\frac{G_{0.5\%NaCl} + G_{1.5\%NaCl}}{2}\right]} \times 100$$

is less than 70%.

3. A device for assessing composition of a plaque as determined by resistance to flow of electrical currents through the plaque, the device comprising:
   an elongated body having a longitudinal axis extending from a proximal end to a distal end, the body having a lumen along the longitudinal axis, the distal end of the body capable of introduction near a plaque at a plaque site;
   a first excitation electrode and a second excitation electrode along the longitudinal axis, both located near the distal end; and
   a first detection electrode and a second detection electrode located along the longitudinal axis and in between the first and second excitation electrodes;
   the at least one of the first and second excitation electrodes in communication with a current source, the current source operable to supply electrical current to the plaque at the plaque site to allow measurement of two or more conductance values at the plaque site by the detection electrodes and to allow calculation of parallel tissue conductance at the plaque site, whereby tissue conductance is the inverse of resistance to current flow, which depends on the composition of the plaque, resulting in a determination of the plaque as being at least partially fatty if the value of % $G_p$ as determined by $$\% G_p = \frac{G_p}{\left[\frac{G_{0.5\%NaCl} + G_{1.5\%NaCl}}{2}\right]} \times 100$$

is less than 70%.

4. The device of claim 3, further comprising: a data acquisition and processing system that receives conductance data from the detection electrodes and determines the conductance of the plaque site.

5. The device of claim 3, further comprising:
   a suction/infusion port located near the distal end, wherein said suction/infusion port is in communication with said lumen, thereby enabling injection of two or more solutions into the plaque site.

6. The device of claim 5, wherein the solution comprises an NaCl solution.

7. The device of claim 5, wherein the lumen is in communication with a source of a solution to be injected therethrough and through the suction/infusion port into a plaque site.

8. A catheter for assessing composition of a plaque, the device comprising:
   an elongated body having a lumen therethrough along a longitudinal length of the elongated body;
   a pair of excitation electrodes located on the elongated body; and
   a pair of detection electrodes located in between the pair of excitation electrodes such that a distance between one detection electrode and its adjacent excitation electrode is equal to the distance between the other detection electrode and its adjacent excitation electrode;
   wherein when two solutions of differing conductive concentrations are introduced to a plaque site through the lumen of the elongated body at different times, two conductance measurements are made by the detection electrodes, resulting in a calculation of parallel tissue conductance at the plaque site to determine plaque composition, resulting in a determination of the plaque as being at least partially fatty if the value of % $G_p$ as determined by $$\% G_p = \frac{G_p}{\left[\frac{G_{0.5\%NaCl} + G_{1.5\%NaCl}}{2}\right]} \times 100$$

is less than 70%.

9. The catheter of claim 8, wherein the detection and excitation electrodes have insulated electrical wire connections that run through the lumen.

10. The catheter of claim 8, wherein the detection and excitation electrodes have electrical wire connections that are embedded within the elongated body such that each wire is insulated from the other wires.

11. A catheter for assessing composition of a plaque, the device comprising:
   an elongated body having a proximal end and a distal end and a lumen therethrough;
   a second body that terminates at the elongated body at a point between the proximal end and the distal end, and having a lumen that joins the lumen of the elongated body;
   a pair of excitation electrodes located at a distal end of the elongated body; and
   a pair of detection electrodes located in between the pair of excitation electrodes;
   wherein when two solutions of differing conductive concentrations are introduced to a plaque site, located near the distal end of the elongated body, through the lumen of the second body, two conductance measurements are made by the detection electrodes, resulting in a calculation of parallel tissue conductance at the plaque site to determine plaque composition, resulting in a determination of the plaque as being at least partially fatty if the value of % $G_p$ as determined by $$\% G_p = \frac{G_p}{\left[\frac{G_{0.5\%NaCl} + G_{1.5\%NaCl}}{2}\right]} \times 100$$

is less than 70%.

12. The catheter of claim 11, wherein the detection and excitation electrodes have insulated electrical wire connections that run through the lumen and proximal end of the elongated body.

13. The catheter of claim 11, wherein the detection and excitation electrodes have electrical wire connections that are embedded within the elongated body such that each wire is insulated from the other wires.

14. The catheter of claim 11, further comprising a guide wire positioned through the proximal end of the elongated body, through the lumen of the elongated body and out of the distal end of the elongated body.

15. A catheter system for assessing composition of a plaque as determined by resistance to flow of electrical currents through the plaque, the system comprising:
   an elongate wire having a longitudinal axis with a proximal end and a distal end;
   a catheter comprising an elongate tube extending from a proximal tube end to a distal tube end, the tube having a lumen and surrounding the wire coaxially;
   a first excitation electrode and a second excitation electrode located along the longitudinal axis of the wire near the distal wire end; and
   a first detection electrode and a second detection electrode along the longitudinal axis of the wire and in between the first and second excitation electrodes,
   the at least one of the first and second excitation electrodes in communication with a current source, the current source operable to supply electrical current to a plaque to allow measurement of two or more conductance values at the plaque by the detection electrodes and to allow calculation of tissue conductance at the plaque site, whereby tissue conductance is the inverse of resistance to current flow, which depends on the composition of the plaque, resulting in a determination of the plaque as being at least partially fatty if the value of % $G_p$ as determined by $$\% G_p = \frac{G_p}{\left[\frac{G_{0.5\%NaCl} + G_{1.5\%NaCl}}{2}\right]} \times 100$$

is less than 70%.

16. The system of claim 15, wherein the wire comprises a pressure wire.

17. The system of claim 15, wherein the wire comprises a guide wire.

18. The system of claim 15, wherein the catheter comprises a guide catheter.

19. The system of claim 15, wherein the wire and the catheter are dimensioned so that a first solution can be infused through the tube lumen.

20. A system for measuring conductance of a plaque site to determine plaque composition, the system comprising:
   a catheter assembly;
   a solution delivery source for injecting a solution through the catheter assembly and into a plaque site;
   a current source; and
   a data acquisition and processing system that receives conductance data from the catheter assembly and calculates parallel tissue conductance at the plaque site to determine plaque composition, resulting in a determination of the plaque as being at least partially fatty if the value of % $G_p$ as determined by $$\% G_p = \frac{G_p}{\left[\frac{G_{0.5\%NaCl} + G_{1.5\%NaCl}}{2}\right]} \times 100$$

is less than 70%.

21. The system of claim 20, wherein the catheter assembly comprises:
   an elongate wire having a longitudinal axis extending from a proximal wire end to a distal wire end;
   a catheter comprising an elongate tube extending from a proximal tube end to a distal tube end, said tube having a lumen along a longitudinal axis of said tube, said tube surrounding the wire coaxially;
   a first excitation impedance electrode and a second excitation impedance electrode along the longitudinal axis of the wire, both located near the distal wire end; and
   a first detection impedance electrode and a second detection impedance electrode along the longitudinal axis of the wire, both located in between the first and second excitation electrodes.

22. A system for determining the composition of a targeted plaque in a plaque site, the system comprising:

a catheter having a proximal end and a distal end, the catheter further comprising a suction/infusion port near the distal end;
a solution delivery source for injecting a solution through the catheter, through the suction/infusion port and into a plaque site containing a plaque;
a current source; and
a data acquisition and processing system that receives conductance data from the catheter and calculates parallel tissue conductance at the plaque site to determine plaque composition, resulting in a determination of the plaque as being at least partially fatty if the value of % $G_p$ as determined by $$\% G_p = \frac{G_p}{\left[\frac{G_{0.5\% NaCl} + G_{1.5\% NaCl}}{2}\right]} \times 100$$

is less than 70%.

23. The system of claim 22, further comprising:
detection electrodes on the distal end of the catheter that transmits the conductance data to the data acquisition and processing system.

24. The system of claim 22, wherein the catheter further comprises a lumen such that the suction/infusion port is in communication with the lumen to allow injection of two or more solutions into the plaque site.

25. The system of claim 24, wherein the lumen is in communication with a source of a solution to be injected therethrough and through the suction/infusion port into a plaque site.

26. A device for assessing composition of a plaque as determined by resistance to flow of electrical currents through the plaque, the device comprising:
an elongate wire having a longitudinal axis with a proximal end and a distal end, wherein the wire is sized and shaped to fit within a lumen of a guide catheter;
a first excitation electrode and a second excitation electrode located along the longitudinal axis of the wire near the distal wire end; and
a first detection electrode and a second detection electrode along the longitudinal axis of the wire and in between the first and second excitation electrodes, wherein the first detection electrode and the second detection electrode are spaced between 0.5 mm and 1.0 mm from each other, and wherein the first detection electrode and the second detection electrode of the wire are operable to measure the two or more conductance values upon infusion of a bolus through the guide catheter;
the at least one of the first and second excitation electrodes in communication with a current source, the current source operable to supply electrical current to a plaque to allow measurement of two or more conductance values at the plaque by the detection electrodes and to allow calculation of tissue conductance at the plaque site, whereby tissue conductance is the inverse of resistance to current flow, which depends on the composition of the plaque.

27. The device of claim 26, wherein the wire is at least one wire chosen from a pressure wire or a guide wire.

28. The device of claim 26, further comprising a data acquisition and processing system that receives conductance data from the first detection electrode and the second detection electrode and calculates parallel tissue conductance at the plaque site to determine plaque composition.

29. A device for assessing composition of a plaque as determined by resistance to flow of electrical currents through the plaque, the device comprising:
an elongate wire having a longitudinal axis with a proximal end and a distal end, wherein the wire is sized and shaped to fit within a lumen of a guide catheter;
a first excitation electrode and a second excitation electrode located along the longitudinal axis of the wire near the distal wire end; and
a first detection electrode and a second detection electrode along the longitudinal axis of the wire and in between the first and second excitation electrodes, wherein the first detection electrode and the second detection electrode are spaced between 0.5 mm and 1.0 mm from each other, and wherein the first detection electrode and the second detection electrode of the wire are operable to measure the two or more conductance values upon infusion of a bolus through the guide catheter;
the at least one of the first and second excitation electrodes in communication with a current source, the current source operable to supply electrical current to a plaque to allow measurement of two or more conductance values at the plaque by the detection electrodes and to allow calculation of tissue conductance at the plaque site, whereby tissue conductance is the inverse of resistance to current flow, which depends on the composition of the plaque, resulting in a determination of the plaque as being at least partially fatty if the value of % $G_p$ as determined by $$\% G_p = \frac{G_p}{\left[\frac{G_{0.5\% NaCl} + G_{1.5\% NaCl}}{2}\right]} \times 100$$

is less than 70%.

30. A device for assessing composition of a plaque, the device comprising:
an elongated body having a lumen therethrough along a longitudinal length of the elongated body;
a pair of excitation electrodes located on the elongated body;
a pair of detection electrodes located in between the pair of excitation electrodes; and
a data acquisition and processing system that receives conductance data from the detection electrodes and determines the conductance of the plaque site;
at least one excitation electrode in communication with a current source, the current source operable to supply electrical current to the plaque at the plaque site to allow measurement of two or more conductance values at the plaque site by the detection electrodes, resulting in a determination of the plaque as being at least partially fatty if the value of % $G_p$ as determined by $$\% G_p = \frac{G_p}{\left[\frac{G_{0.5\% NaCl} + G_{1.5\% NaCl}}{2}\right]} \times 100$$

is less than 70%.

31. The device of claim 30, further comprising:
a suction/infusion port located near a distal end of the elongated body, wherein said suction/infusion port is in communication with said lumen, thereby enabling injection of two or more solutions into the plaque site.

* * * * *